United States Patent
Jun et al.

(10) Patent No.: US 10,751,392 B2
(45) Date of Patent: Aug. 25, 2020

(54) PHARMACEUTICAL COMPOSITION FOR TREATING SARCOPENIA INCLUDING GLUCAGON-LIKE PEPTIDE-1 RECEPTOR AGONIST

(71) Applicant: IMMUNOFORGE CO., LTD., Gyeonggi-do (KR)

(72) Inventors: Hee Sook Jun, Incheon (KR); Eun Young Park, Incheon (KR); Yeon Hee Hong, Sejong (KR)

(73) Assignee: IMMUNOFORGE CO., LTD., Gyeonggi-Do (KR)

( * ) Notice: Subject to any disclaimer, the term of this patent is extended or adjusted under 35 U.S.C. 154(b) by 107 days.

(21) Appl. No.: 15/577,299

(22) PCT Filed: May 27, 2016

(86) PCT No.: PCT/KR2016/005615
§ 371 (c)(1),
(2) Date: Nov. 27, 2017

(87) PCT Pub. No.: WO2016/190697
PCT Pub. Date: Dec. 1, 2016

(65) Prior Publication Data
US 2018/0153964 A1     Jun. 7, 2018

(30) Foreign Application Priority Data

May 28, 2015  (KR) .................. 10-2015-0074985

(51) Int. Cl.
| | |
|---|---|
| A61K 38/26 | (2006.01) |
| A61K 9/48 | (2006.01) |
| A61K 9/20 | (2006.01) |
| A61K 47/30 | (2006.01) |
| A61K 38/16 | (2006.01) |
| A61K 9/16 | (2006.01) |
| A61K 48/00 | (2006.01) |
| A61P 21/00 | (2006.01) |
| A61K 38/22 | (2006.01) |

(52) U.S. Cl.
CPC ............... *A61K 38/26* (2013.01); *A61K 9/16* (2013.01); *A61K 9/20* (2013.01); *A61K 9/48* (2013.01); *A61K 38/16* (2013.01); *A61K 38/22* (2013.01); *A61K 47/30* (2013.01); *A61K 48/00* (2013.01); *A61P 21/00* (2018.01)

(58) Field of Classification Search
CPC ...................................................... A61K 38/26
See application file for complete search history.

(56) References Cited

U.S. PATENT DOCUMENTS

| | | | |
|---|---|---|---|
| 6,872,700 B1 | 3/2005 | Young et al. | |
| 8,906,851 B2 * | 12/2014 | Fineman .............. | A61K 9/0019 514/6.8 |

FOREIGN PATENT DOCUMENTS

| | | |
|---|---|---|
| JP | 2013-507341 A | 3/2013 |
| JP | 5695097 B2 | 7/2013 |
| KR | 10-0837363 B1 | 6/2008 |
| KR | 10-1439783 B1 | 9/2014 |
| WO | WO 2006/081997 | 8/2006 |
| WO | WO 2007/088123 | 8/2007 |
| WO | WO 2014-096148 A1 | 6/2014 |

OTHER PUBLICATIONS

Ikejima et al., Diabetes, 67:supplement 1, ( 2018).*
Perfetti et al., Eur. J. Endocr. 143, 717-725,( 2000).*
Gutniak et al., New England J. Med. 30 326:1316-1322, (1992).*
Centrone et al., Current Diabetes Reviews, 10: 231-237,( 2014).*
Amato et al. 2014. Exogenous glucagon-like peptide 1 reduces contractions in human colon circular muscle, *Journal of Endocrinology*, 221(1):29-37.
Cetrone et al. 2014. Effects of the antidiabetic drugs on the age-related atrophy and sarcopenia associated with Diabetes Type II. *Current Diabetes Review*, 10(4):231-237.
International Search Report dated Aug. 8, 2016 for International Application No. PCT/KR2016/005615 filed May 27, 2016, 8 pages.
Written Opinion dated Aug. 8, 2016 for International Application No. PCT/KR2016/005615 filed May 27, 2016, 6 pages.
Chuan-An Shen et al: "Effects of glucagon-like peptide 1 on glycemia control and its metabolic consequence after severe thermal injurystudies in an animal model", Surgery, Mosby, Inc, US, vol. 149, No. 5, Nov. 24, 2010 (Nov. 24, 2010), pp. 635-644, XP028193515.
Elahi D, et al., GLP-1(32-36)amide, a novel pentapeptide cleavage product of GLP-1, modulates whole body glucose metabolism in dogs, Peptides, Jun. 14, 2014, vol. 59, p. 20-24.
Fanzani A, et al., Molecular and cellular mechanisms of skeletal muscle atrophy: an update, Journal of Cachexia, Sarcopenia and Muscle, Jun. 7, 2012, vol. 3, No. 3, p. 163-179.

(Continued)

*Primary Examiner* — Gyan Chandra
(74) *Attorney, Agent, or Firm* — Knobbe, Martens, Olson & Bear LLP (57) ABSTRACT

Provided are a pharmaceutical composition for preventing or treating muscle atrophy or sarcopenia including glucagon-like peptide-1 (GLP-1), a GLP-1 fragment, a GLP-1 secretion enhancer, a GLP-1 degradation inhibitor, a GLP-1 receptor (GLP-1R) agonist, or exendin-4, and a method of treating muscle atrophy or sarcopenia by using the pharmaceutical composition. When the pharmaceutical composition for preventing or treating muscle atrophy or sarcopenia provided in the present invention is administered to a subject having sarcopenia or muscle atrophy, reduced body weight, skeletal muscle mass, and grip strength, which are caused by sarcopenia or muscle atrophy, and expression levels of genes involved in muscle production may be restored to normal states, and therefore, the composition may be widely applied to the development of effective therapeutic agents for sarcopenia or muscle atrophy.

9 Claims, 6 Drawing Sheets
Specification includes a Sequence Listing.

(56) References Cited

OTHER PUBLICATIONS

Hisashi Kuwata, Hiroshi Seino, DPP-4 inhibitor, hepatobiliary pancreas, Nov. 2012, vol. 65, No. 5, p. 809-816.

Junichiro Miyagawa, Mitsuyoshi Namba, DPP-4 inhibitor (incretin enhancer), Japanese clinical, 2012, 70, extra No. 3 (latest clinical diabetes studies (upper), p. 682-688.

Knippenberg S, et al., Intracerebroventricular injection of encapsulated human mesenchymal cells producing glucagon-like peptide 1 prolongs s urvival in a mouse model of ALS, PLoS One, Jun. 20, 2012, vol. 7 , No. 6, e36857, doi: 10.1371/journal.pone.0036857.

Li Y, et al., Exendin-4 ameliorates motor neuron degeneration in cellular and animal models of amyotrophic lateral sclerosis, PLoS One, Feb. 23, 2012, vol. 7, No. 2, e32008, doi: 10.1371/journal.pone.0032008.

Sun H, et al., Therapeutic potential of N-acetyl-glucagon-like peptide-1 in primary motor neuron cultures derived from non-transgenic and SOD 1-G93A ALS mice, Cellular and Molecular Neurobiology, 2013, vol. 33 , No. 3, p. 347-357.

Office Action issued in JP application No. 2018-514760, dated Oct. 9, 2018.

Supplemental Search Report issued in EP application No. 1680033.6, dated Nov. 30, 2018.

\* cited by examiner

SEQUENCE LISTING

```
<160> NUMBER OF SEQ ID NOS: 2

<210> SEQ ID NO 1
<211> LENGTH: 39
<212> TYPE: PRT
<213> ORGANISM: Artificial Sequence
<220> FEATURE:
<223> OTHER INFORMATION: recombinant Exendin-4

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 2
<211> LENGTH: 5
<212> TYPE: PRT
<213> ORGANISM: Artificial Sequence
<220> FEATURE:
<223> OTHER INFORMATION: GLP-1(32-36)amide

<400> SEQUENCE: 2

Leu Val Lys Gly Arg
1               5
```

PHARMACEUTICAL COMPOSITION FOR TREATING SARCOPENIA INCLUDING GLUCAGON-LIKE PEPTIDE-1 RECEPTOR AGONIST

CROSS-REFERENCE TO RELATED APPLICATIONS

This application is a U.S. National Phase Application of PCT International Application No. PCT/KR2016/005615, filed on May 27, 2016, designating the United States of America, which is an International Application of and claims the benefit of priority to Korean Patent Application No. 10-2015-0074985, filed on May 28, 2015.

SEQUENCE LISTING STATEMENT

The present application contains a Sequence Listing, which is being submitted via EFS-Web on even date herewith. The Sequence Listing is submitted in a file entitled "Sequence Listing HAN032-001APC.txt," which was created on Nov. 27, 2017, and is approximately 4 kb in size. This Sequence Listing is hereby incorporated by reference.

TECHNICAL FIELD

The present invention relates to a pharmaceutical composition for treating sarcopenia including a glucagon-like peptide-1 receptor agonist, and more particularly, to a pharmaceutical composition for preventing or treating muscle atrophy or sarcopenia including glucagon-like peptide-1 (GLP-1), a GLP-1 fragment, a GLP-1 secretion enhancer, a GLP-1 degradation inhibitor, a GLP-1 receptor (GLP-1R) agonist, or exendin-4, and a method of treating muscle atrophy or sarcopenia by using the pharmaceutical composition.

BACKGROUND ART

Sarcopenia caused by degeneration of spinal nerve, motor nerve, or skeletal muscle fiber is a representative intractable diseases of which the etiology has not yet been clarified. According to studies conducted thus far, it is known that contraction of skeletal muscles does not occur due to degeneration of motor nerves inducing contraction of skeletal muscles, normal contraction of skeletal muscles does not occur due to reduced expression (sarcopenia) or modification of proteins involved in muscle contraction in the skeletal muscles, and motor nerves or skeletal muscles are modified to fibrous tissues in the long term. As such, since the underlying cause of sarcopenia has not been identified, and methods capable of preventing or restoring degeneration of motor nerves or skeletal muscles have not been developed, studies are presently underway in order to develop a method of slowing the progression of sarcopenia.

As a method of slowing the progression of sarcopenia, a method of inhibiting muscle atrophy caused by degenerative or progressive modification of myocytes, which is a kind of sarcopenia, is mainly used. For example, WO 2007/088123 discloses a therapeutic agent for muscle atrophy including a nitrooxyderivative as an active ingredient, and WO 2006/081997 discloses a therapeutic agent for muscle atrophy including atraric acid or a derivative thereof as an active ingredient. However, since these therapeutic agents including the compounds as the active ingredients act on smooth muscles or cardiac muscles which are not associated with muscle atrophy, as well as on skeletal muscles in which muscle atrophy occurs, a variety of major or minor side effects may be caused, and therefore, the therapeutic agents do not have practical application. Although hormone agents have side effects, their side effects are remarkably reduced as compared with chemical agents, and the hormone agents have bio-friendly properties. Therefore, development of hormone-like agents is being accelerated.

Meanwhile, muscle atrophy is a disease in which muscles of the legs and arms are atrophied, and represented by amyotrophic lateral sclerosis and spinal progressive muscular atrophy, which are known as diseases caused by progressive modification of motor nerve fibers and cells in the spinal cord.

Specifically, spinal muscular atrophy is known as a genetic disorder and neuromuscular disease caused by modification of motor neurons in the spinal cord. Further, amyotrophic lateral sclerosis is characterized by intractable, irreversible neurodegenerative changes due to the death of upper motor neurons and lower motor neurons in the cerebrum and spinal cord, and its main cause is known to be lack of nerve growth factor and neuritis.

DISCLOSURE

Technical Problem

The present inventors have made intensive efforts to develop an agent capable of effectively treating muscle atrophy or sarcopenia or effectively slowing progression thereof, and as a result, they found that exendin-4, which is a kind of glucagon-like peptide-1 receptor agonist, may alleviate symptoms of sarcopenia, thereby completing the present invention.

Technical Solution

An object of the present invention is to provide a pharmaceutical composition for preventing or treating muscle atrophy or sarcopenia.

Another object of the present invention is to provide a method of treating muscle atrophy or sarcopenia by using the pharmaceutical composition.

Advantageous Effects

When a pharmaceutical composition for preventing or treating muscle atrophy or sarcopenia provided in the present invention is administered to a subject having sarcopenia or muscle atrophy, reduced body weight, skeletal muscle mass, and grip strength, which are caused by sarcopenia or muscle atrophy, and expression levels of genes involved in muscle production may be restored to normal states, and therefore, the composition may be widely applied to the development of effective therapeutic agents for sarcopenia or muscle atrophy.

BEST MODE

The present inventors have conducted various studies to develop hormone agents which may effectively treat sarcopenia or effectively slow progression thereof, and have focused on known hormone agents. These hormone agents are pharmaceutical compositions which were approved as having minimal side effects through predetermined levels of preclinical and clinical trials, and thus it was expected that selection of agents capable of treating or slowing sarcopenia from the hormone agents may solve the problems due to side effects. Accordingly, agents capable of treating or slowing sarcopenia were screened from the known hormone agents, and as a result, exendin-4, represented as a glucagon-like peptide-1 receptor agonist, was investigated.

Exendin-4, a kind of glucagon-like peptide-1 receptor agonist, is a peptide hormone agent that plays a similar role to GLP-1, a glucagon analogue, and was developed to treat diabetes. Exendin-4 was administered to an animal in which sarcopenia was artificially induced, and its effects on sarcopenia were analyzed. As a result, it was found that muscular properties caused by sarcopenia, such as reduced body weight, skeletal muscle mass, grip strength, etc., were restored, expression of muscle protein-destroying genes was decreased, and expression of muscle protein-producing genes was increased. Further, other agonists of GLP-1R, which is a glucagon-like peptide-1 receptor, an analogue thereof, or an inhibitor inhibiting degradation of glucagon-like peptide-1 were expected to show equivalent levels of the effects.

As such, it was demonstrated that exendin-4, represented as a glucagon-like peptide-1 receptor agonist, has a novel effect of treating or slowing sarcopenia, in addition to the therapeutic effect on diabetes, and this novel effect has never been disclosed until now, and was demonstrated by the present inventors for the first time.

To achieve the above objects, an aspect of the present invention provides a pharmaceutical composition for preventing or treating muscle atrophy or sarcopenia including any one selected from the group consisting of glucagon-like peptide-1 (GLP-1), a GLP-1 fragment, a GLP-1 secretion enhancer, a GLP-1 receptor (GLP-1R, glucagon-like peptide-1 receptor) agonist, a GLP-1 secretion enhancer, a GLP-1 degradation inhibitor, and exendin-4.

As used herein, the term "glucagon-like peptide-1 (GLP-1)" is an incretin derived from a transcription product of a proglucagon gene, which is a prohormone, and is a hormone secreted by intestinal L cells by stimulation of intestinal nutrients or blood glucose level. Its major function is known to be stimulation of insulin secretion. For this reason, GLP-1 has been studied and developed as a drug capable of effectively reducing blood glucose in the treatment of diabetes.

GLP-1 consists of 30 amino acids, and an amino acid sequence of GLP-1 is known to be 100% homologous in all mammals. It is known that glucagon is produced from proglucagon in pancreatic a cells by a post-transcriptional process, and GLP-1 is produced in L cells of the ileum and large intestine.

As used herein, the term "GLP-1 fragment" refers to an amino acid sequence which is derived from the amino acid sequence of GLP-1 and prepared by any one method of substitution, addition, deletion, and modification of some amino acids in GLP-1, or a combination thereof. The GLP-1 fragment may be prepared by a method known to those skilled in the art. With respect to the objects of the present invention, any one may be included in the "GLP-1 fragment" of the present invention, as long as it is derived from GLP-1 and has the effects on muscle atrophy or sarcopenia. The GLP-1 fragment may include 5 or more, 10 or more, 15 or more, or 20 or more amino acids of the GLP-1 sequence. Specifically, the GLP-1 fragment may be GLP-1(28-36) amide or GLP-1(32-36)amide, and more specifically, the GLP-1 fragment may be GLP-1(32-36)amide (LVKGR amide) prepared by 5 amino acids of GLP-1, but is not limited thereto.

According to a specific embodiment of the present invention, the GLP-1(32-36)amide may have a sequence of SEQ ID NO: 2.

The present inventors confirmed that GLP-1(32-36) amide, a GLP-1 fragment, has a therapeutic effect on muscle atrophy or sarcopenia by increasing the body weight, muscle mass, and grip strength, decreasing expression of myostatin and increasing expression of MyoD in dexamethasone-treated mice, suggesting that therapeutic effects on muscle atrophy or sarcopenia may be obtained by the GLP-1 fragment (FIGS. 6 to 9).

As used herein, the term "GLP-1 receptor (GLP-1R, glucagon-like peptide-1 receptor)" refers to a receptor protein capable of binding with GLP-1 (glucagon-like peptide-1), which is a kind of gastrointestinal hormone derived from a transcript of a glucagon gene, and plays a role in reducing blood glucose levels. Specifically, the receptor binds with GLP-1 to increase transcription and expression of insulin gene via up-regulation of pancreatic duodenal homeobox-1 (PDX-1) which is a transcription factor.

As used herein, the term "GLP-1 receptor agonist (GLP-1R agonist)" refers to a substance or drug that binds to the GLP-1 receptor to act similarly to GLP-1, or a molecule that increases activity of a receptor site, and is also called an effector. The agonist is currently used as a therapeutic agent for type 2 diabetes, as its effect of increasing insulin secretion by binding to GLP-1 receptor was revealed.

Examples of the receptor agonist include GLP-1 and glucagon, which are known as natural agonists. In addition, there are liraglutide, exendin-4, lixisenatide, etc.

With respect to the objects of the present invention, the GLP-1 receptor agonist includes a substance that binds to the GLP-1 receptor, like GLP-1, and has similar activity to GLP-1 via a similar signaling pathway, and may have a therapeutic effect on muscle atrophy or sarcopenia by increasing muscle mass and strength.

As used herein, the term "exendin-4" refers to a peptide that functions as a GLP-1 receptor agonist, and has a sequence consisting of 39 amino acids and a molecular weight of about 4 kDa. Since exendin-4 shows effects of rapidly regulating blood glucose levels, decreasing insulin resistance and glucagon levels, and promoting growth of pancreatic beta cells stimulating insulin production, it is used as a major therapeutic agent for diabetes with insulin resistance. An amino acid sequence of exendin-4 has an amino acid sequence of SEQ ID NO: 1, but is not particularly limited thereto.

In the present invention, exendin-4 is used an active ingredient of the pharmaceutical composition for treating sarcopenia, and exendin-4 may exhibit effects of increasing the body weight and skeletal muscle mass, inhibiting expression of muscle protein-destroying genes, and increasing expression of muscle protein-producing genes with respect to animals having sarcopenia. In this regard, examples of the muscle protein-destroying genes may include, but are not particularly limited to, genes encoding proteins such as myostatin, atrogin-1, MuRF1 (Muscle RING-finger protein-1), etc., and examples of the muscle protein-producing genes may include, but are not particularly limited to, genes encoding proteins such as MyoD, myogenin, etc.

The above-described therapeutic effects of exendin-4 on sarcopenia were unknown until now, and were demonstrated by the present inventors for the first time.

The present inventors confirmed that exendin-4 shows the effects of increasing the body weight and skeletal muscle mass, inhibiting expression of muscle protein-destroying genes, and increasing expression of muscle protein-producing genes, and thus exendin-4 may be used in the prevention and treatment of muscle atrophy or sarcopenia.

Meanwhile, exendin-4 is an example of the GLP-1 receptor agonist, and has similar activity to GLP-1 via binding with the GLP-1 receptor.

In the present invention, therefore, the GLP-1R agonist or analogue thereof shows an equivalent effect to exendin-4, and is thereby used as an active ingredient of the pharmaceutical composition for preventing or treating sarcopenia or muscle atrophy.

As used herein, the term "GLP-1 secretion enhancer" refers to an agent capable of increasing GLP-1 secretion. Specific examples of the "GLP-1 secretion enhancer" may include G-protein coupled receptor 119 agonist, but are not limited thereto.

In the present invention, the GLP-1 secretion enhancer exhibits equivalent effects to GLP-1 or exendin-4 (the effects of increasing the skeletal muscle mass, inhibiting expression of muscle protein-destroying genes, and increasing expression of muscle protein-producing genes) by increasing GLP-1 secretion, and therefore, it may be used as an active ingredient of the pharmaceutical composition for preventing or treating sarcopenia or muscle atrophy.

As used herein, the term "GLP-1 degradation inhibitor" refers to an agent capable of maintaining the actions of GLP-1 by inhibiting GLP-1 degradation. The GLP-1 degradation inhibitor is a DPP-4 inhibitor, etc., but is not particularly limited thereto.

According to a specific embodiment of the present invention, the GLP-1 degradation inhibitor may be a DPP-4 (dipeptidyl peptidase-4) inhibitor.

As used herein, the term "DPP-4 (dipeptidyl peptidase-4) inhibitor" refers to an enzyme inhibiting DPP-4 enzyme which is known to degrade GLP-1, and maintains high concentrations of GLP-1 by inhibiting DPP-4. Specifically, the inhibitor may be vidagliptin, sitagliptin, or saxagliptin, and more specifically, sitagliptin, but is not limited thereto.

In the present invention, the GLP-1 degradation inhibitor acts to maintain GLP-1 concentration by inhibiting degradation of GLP-1, and consequently, it may have the therapeutic effect on muscle atrophy or sarcopenia, similar to GLP-1 or exendin-4.

The present inventors confirmed that sitagliptin shows effects of increasing the body weight, skeletal muscle mass, and grip strength, inhibiting myostatin expression, and increasing MyoD expression in dexamethasone-treated mice, and therefore, sitagliptin exhibits therapeutic effects on muscle atrophy or sarcopenia (FIGS. 6 to 9).

As used herein, the term "muscle atrophy" collectively refers to a disease in which muscles of the legs and arms are gradually atrophied almost symmetrically, and muscle atrophy may accompany the occurrence of cancer, aging, renal diseases, genetic diseases, and various chronic diseases. Muscle atrophy is represented by amyotrophic lateral sclerosis (Lou Gehrig's disease), spinal progressive muscular atrophy, etc.

As used herein, the term "sarcopenia" refers to gradual weakness of density and functions of muscles, and is known to be caused by progressive modification and degradation of motor neurons or myocytes in the spinal cord or diencephalon. In particular, muscle loss due to aging is called age-related sarcopenia.

As a method of slowing the progression of sarcopenia, a method of inhibiting muscle atrophy, which is a kind of sarcopenia, is mainly used. The present inventors confirmed that exendin-4, GLP-1(32-36)amide, and sitagliptin show the effects of increasing body weight, muscle mass, and grip strength, decreasing myostatin expression, and increasing MyoD expression in dexamethasone-induced muscle atrophy mouse models, thereby having therapeutic effects on sarcopenia as well as muscle atrophy.

In the present invention, the muscle atrophy or sarcopenia may be treated by using glucagon-like peptide-1, the GLP-1 fragment, the GLP-1 secretion enhancer, the GLP-1 degradation inhibitor, the GLP-1 receptor agonist, or exendin-4, and therapeutic effects thereof may be equivalently applied to muscle atrophy as well as sarcopenia caused variously by, for example, cancer, aging, renal diseases, etc.

Figure 3:
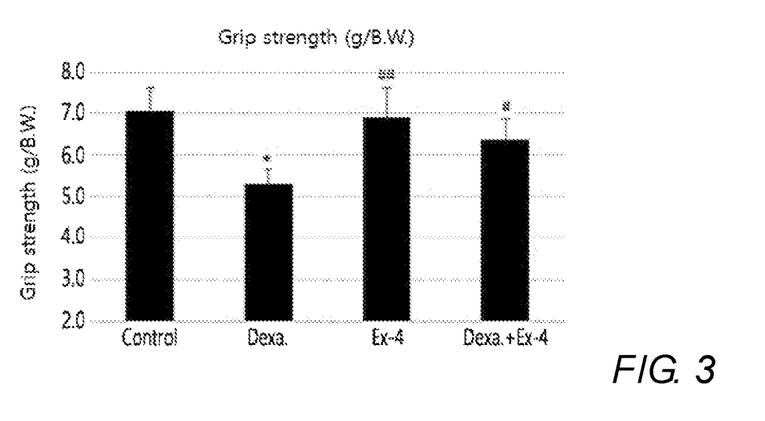
FIG. 3 is a graph showing results of comparing grip strengths which were measured in control mice, comparative mice, muscle atrophy-induced mice, and muscle atrophy-treated mice.
Figure 4:
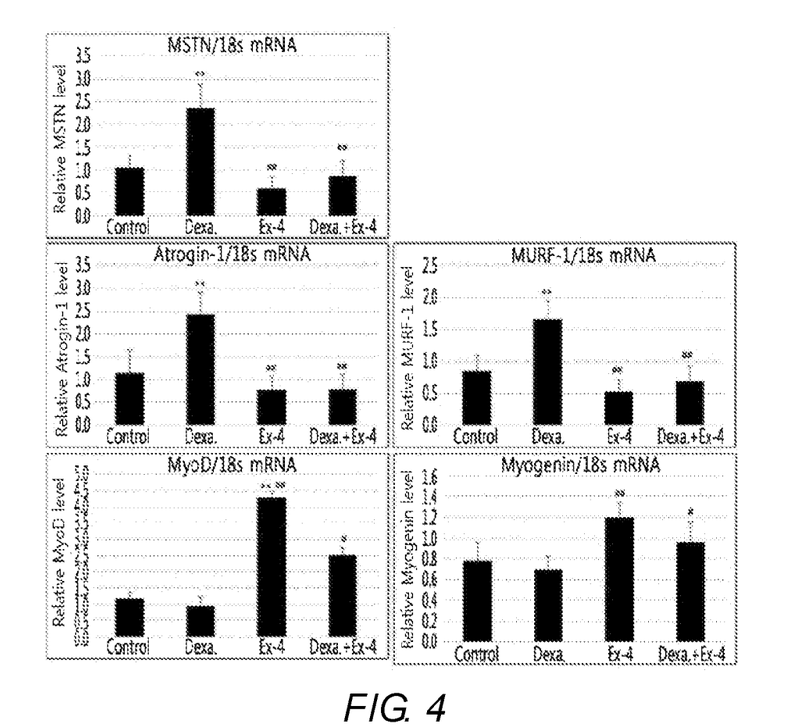
FIG. 4 is a graph showing results of comparing expression levels of muscle protein-destroying genes (myostatin, atrogin-1, and MuRF1) and muscle protein-producing genes (MyoD and myogenin) in control mice, comparative mice, muscle atrophy-induced mice, and muscle atrophy-treated mice.

According to an Example of the present invention, dexamethasone-induced sarcopenia or muscle atrophy mice and sarcopenia or muscle atrophy mice as animal models were treated with a vehicle (PBS) or exendin-4, respectively, and these mice were used to examine the effect of exendin-4 on the mouse models. As a result, when the mice were treated with exendin-4, reduced body weight was restored (FIG. 1), and reduced skeletal muscle mass was restored (FIG. 2), reduced grip strength was restored (FIG. 3), and increased expression levels of muscle protein-destroying genes (myostatin, atrogin-1, and MuRF1) by dexamethasone were decreased whereas expression levels of muscle protein-producing genes (MyoD and Myogenin) were increased (FIG. 4).

Therefore, it can be seen that exendin-4, identified as a glucagon-like peptide-1 receptor agonist, may be used as an active ingredient of the pharmaceutical composition for treating muscle atrophy or sarcopenia.

The composition of the present invention may be prepared in the form of a pharmaceutical composition for preventing or treating inflammatory diseases further including appropriate carriers, excipients, or diluents which are commonly used in the preparation of pharmaceutical compositions. Specifically, the pharmaceutical composition may be formulated according to common methods into oral dosage forms such as powders, granules, tablets, capsules, suspensions, emulsions, syrups, aerosols, etc., external dosage forms, suppositories, or sterile injectable solutions. In the present invention, the carriers, excipients, and diluents included in the pharmaceutical composition may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, and minerals. These formulations may be prepared by using a commonly used diluent or excipient, such as a filler, an extender, a binder, a wetting agent, a disintegrant, a surfactant, etc. Examples of a solid formulation for oral administration include a tablet, a pill, a powder, a granule a capsule, etc. These solid formulations are prepared by mixing the extract or a fraction thereof with at least one excipient, for example, starch, calcium carbonate, sucrose, lactose, gelatin, etc. A lubricant such as magnesium stearate or talc may be also used in addition to the simple excipient. Examples of a liquid formulation for oral administration include a suspension, a solution for internal use, an emulsion, a syrup, etc. The liquid formulation may include, in addition to liquid paraffin or water, a commonly available simple diluent, various excipients, such as a wetting agent, a sweetener, an aromatic, a preservative, etc. A formulation for parenteral administration may include a sterilized aqueous solution, a non-aqueous solvent, a suspension, an emulsion, a lyophilized formulation, and a suppository. The non-aqueous solvent and the suspension may be propylene glycol, polyethylene glycol, a plant oil such as olive oil, or an injectable ester such as ethyloleate. A base for the suppository formulation may be witepsol, macrogol, tween 61, cacao butter, laurin butter, glycerogellatin, etc.

A content of the glucagon-like peptide-1 receptor agonist in the pharmaceutical composition of the present invention may be, but is not particularly limited to, for example, 0.0001% by weight to 10% by weight, and for another example, 0.01% by weight to 3% by weight.

The pharmaceutical composition of the present invention may be administered in a pharmaceutically effective amount. As used herein, the term "pharmaceutically effective amount" refers to an amount sufficient to treat or prevent diseases at a reasonable benefit/risk ratio applicable to any medical treatment or prevention, and the effective dosage level may be determined depending on factors including severity of the disease, activity of the drug, a patient's age, body weight, health, and sex, sensitivity to the drug, administration time, administration route, and excretion rate of the composition of the present invention, duration of treatment, drugs used simultaneously or in combination with the composition of the present invention, and other factors known in the medical field. The pharmaceutical composition of the present invention may be administered alone or in combination with other known therapeutic agents for sarcopenia. It is important to administer the composition in a minimum amount that may exhibit a maximum effect without causing side effects, in view of all of the above-described factors.

An administration dose of the pharmaceutical composition of the present invention may be determined by a skilled person in the art considering the intended use(s), severity of disease(s), age, body weight, sex, and anamnesis of a patient, or kinds of ingredients used as active ingredient(s), etc. For example, the pharmaceutical composition of the present invention may be administered in an amount of about 0.1 ng/kg to about 100 mg/kg per adult, preferably about 1 ng/kg to about 10 mg/kg per adult, and administration frequency of the composition of the present invention is not particularly limited, but the composition of the present invention may be administered once daily or in divided doses. The administration dose does not limit the scope of the present invention in any aspect.

Another aspect of the present invention provides a method of treating sarcopenia or muscle atrophy, including administering a pharmaceutically effective amount of the pharmaceutical composition to a subject with sarcopenia or muscle atrophy excluding humans.

As used herein, the term "subject" includes all mammalian animals including mice, livestock, and humans, or cultured fish which may have sarcopenia or muscle atrophy or have already had sarcopenia or muscle atrophy, without limitation.

The pharmaceutical composition for treating muscle atrophy or sarcopenia of the present invention may be administered via any of the common routes, as long as it is able to reach a desired tissue. The pharmaceutical composition of the present invention may be administered intraperitoneally, intravenously, intramuscularly, subcutaneously, intradermally, orally, intranasally, intrapulmonarily, or intrarectally according to the desired purpose, but the present invention is not particularly limited thereto. However, since the glucagon-like peptide-1 receptor agonist may be denatured by gastric acid upon oral administration, active ingredients of a composition for oral administration should be coated or formulated for protection against degradation in the stomach. In addition, the composition may be administered using a certain apparatus capable of transporting the active ingredients into a target cell.

Still another aspect of the present invention provides use of the pharmaceutical composition in the preparation of a drug for preventing or treating muscle atrophy or sarcopenia.

MODE FOR INVENTION

Hereinafter, the present invention will be described in more detail with reference to Examples. However, these Examples are for illustrative purposes only, and the scope of the present invention is not intended to be limited by these Examples.

Example 1: Effect of Exendin-4 on Body Weight of Muscle Atrophy-Induced Animal

It is known that muscle atrophy is caused by chronic diseases (chronic renal failure, chronic heart failure, chronic obstructive disease, etc.), and caused by administration of a high dose of a drug such as dexamethasone. Thus, animal models (C57BL/6J male mice) were treated with dexamethasone to prepare sarcopenia models. When sarcopenia occurred, effects of exendin-4 were investigated.

In detail, control mice which were not administered with dexamethasone or exendin-4, mice in which muscle atrophy was induced by intraperitoneal injection of dexamethasone (200 mg/kg) for 8 days, comparative mice which were intraperitoneally injected with exendin-4 (100 ng/mouse) for 12 days, and mice in which muscle atrophy was treated by intraperitoneal injection of exendin-4 (100 ng/mouse) for 12 days following intraperitoneal injection of dexamethasone (200 mg/kg) for 8 days were prepared. While these mice were raised for 20 days, changes in their body weights were measured (FIG. 1).

Figure 1:
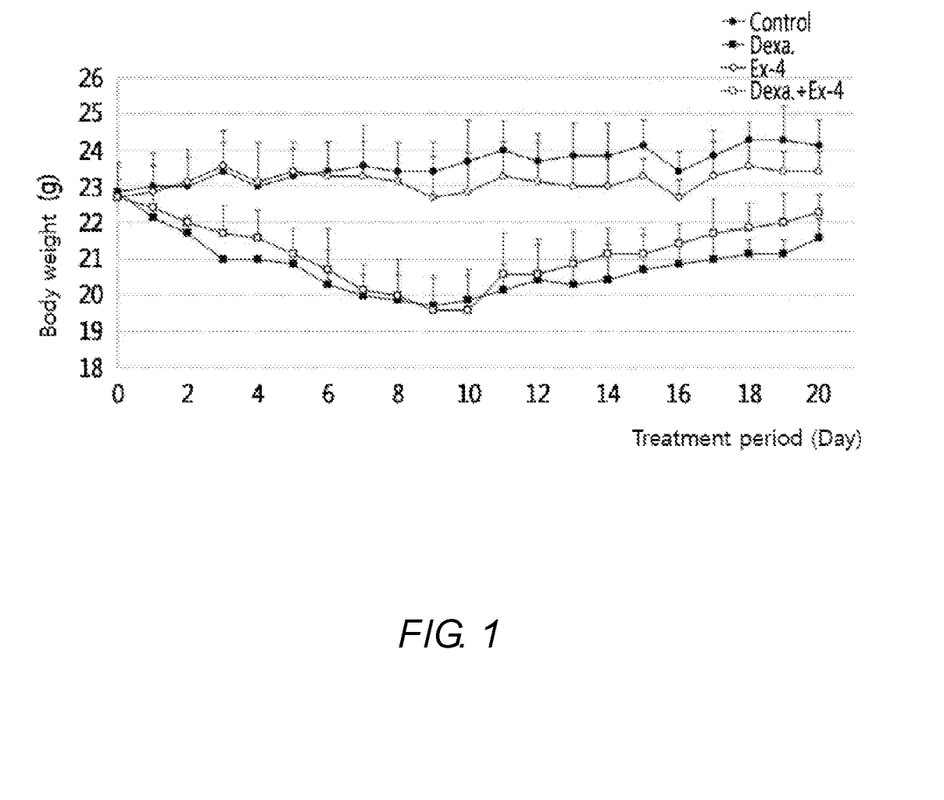
FIG. 1 is a graph showing changes in the body weights which were measured in control mice, comparative mice, muscle atrophy-induced mice, and muscle atrophy-treated mice while they were raised for 20 days.

FIG. 1 is a graph showing changes in the body weights which were measured in control mice, comparative mice, muscle atrophy-induced mice, and muscle atrophy-treated mice while they were raised for 20 days. As shown in FIG.

1, increase in the body weight was observed in the mice treated with combination of dexamethasone and exendin-4, compared to the mice treated with dexamethasone alone, from the elapsed time of 11 days.

Therefore, it can be seen that exendin-4 exhibits the effect of improving symptoms of muscle atrophy-induced mice.

Example 2: Effect of Exendin-4 on Muscle Mass of Muscle Atrophy-Induced Animal

The control mice (control), dexamethasone-induced muscle atrophy mice, exendin-4-treated comparative mice, and muscle atrophy-treated mice treated with exendin-4 following treatment of dexamethasone, which were prepared in Example 1, were sacrificed, and total weights of the skeletal muscles of the respective mice were measured. Quadratus muscles, gastrocnemius muscles, tibialis anterior muscles, soleus muscles, and extensor digitorum longus muscles constituting the skeletal muscles were each separated, and their weights were compared (FIG. 2).

Figure 2:
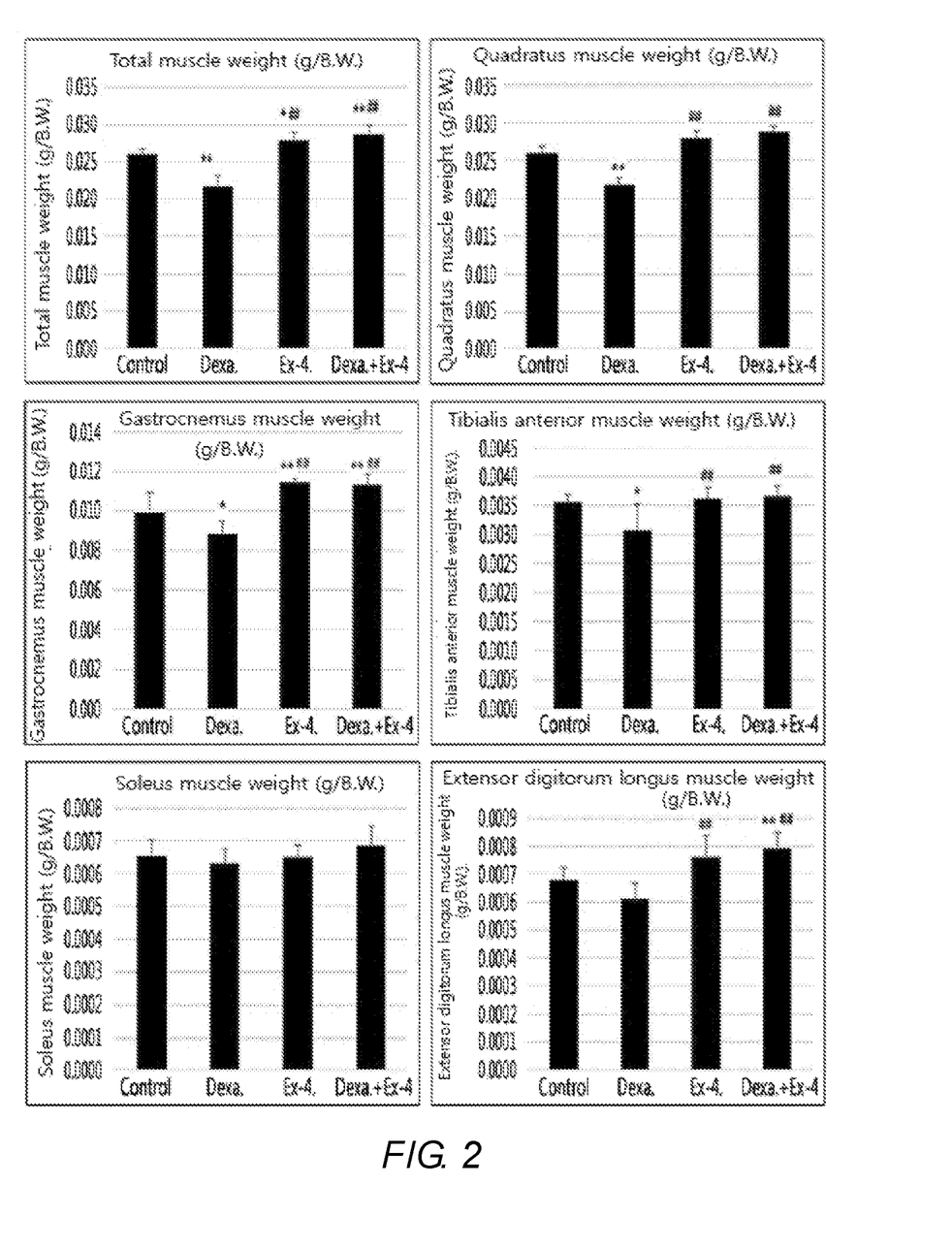
FIG. 2 is a graph showing results of comparing weights of respective skeletal muscles which were obtained from control mice, comparative mice, muscle atrophy-induced mice, and muscle atrophy-treated mice.

FIG. 2 is a graph showing results of comparing weights of respective skeletal muscles which were obtained from control mice, comparative mice, muscle atrophy-induced mice, and muscle atrophy-treated mice. As shown in FIG. 2, muscle atrophy-induced mice showed a reduction in the muscle mass of all kinds of skeletal muscles, as compared with the control and comparative group, whereas muscle atrophy-treated mice showed increased muscle mass similar to that of the control or comparative group.

Example 3: Effect of Exendin-4 on Grip Strength of Muscle Atrophy-Induced Animal The control mice (control), dexamethasone-induced muscle atrophy mice, exendin-4-treated comparative mice, and muscle atrophy-treated mice treated with exendin-4 following treatment of dexamethasone, which were prepared in Example 1, were subjected to measurement of grip strength to investigate whether muscle functions were recovered (FIG. 3). In this regard, a force measured by a grip strength machine when all of the paws of a mouse were pulled with the same force was considered as the grip strength.

FIG. 3 is a graph showing results of comparing grip strengths which were measured in control mice, comparative mice, muscle atrophy-induced mice, and muscle atrophy-treated mice. As shown in FIG. 3, it was found that the muscle atrophy-induced mice showed the lowest level of grip strength whereas muscle atrophy-treated mice showed a lightly lower level of grip strength than the control and comparative mice, but a remarkably higher level of grip strength than the muscle atrophy-induced mice.

Example 4: Effect of Exendin-4 on Expression Levels of Muscle Protein-Producing Genes and Muscle Protein-Destroying Genes in Muscle Atrophy-Induced Animal It is known that when muscle atrophy occurs, expression of muscle protein-destroying genes (myostatin, atrogin-1, and MuRF1) is increased and expression of muscle protein-producing genes (MyoD and myogenin) is decreased; thus, this was to be examined. That is, muscle tissues were removed from the control mice (control), dexamethasone-induced muscle atrophy mice, exendin-4-treated comparative mice, and muscle atrophy-treated mice treated with exendin-4 following treatment of dexamethasone, which were prepared in Example 1, and total RNAs were obtained from the muscle tissues. cDNAs were synthesized therefrom, each gene was amplified from the synthesized cDNA by PCR, and changes in the expression levels thereof were compared (FIG. 4).

FIG. 4 is a graph showing results of comparing expression levels of muscle protein-destroying genes (myostatin, atrogin-1, and MuRF1) and muscle protein-producing genes (MyoD and myogenin) in the muscles of control mice, comparative mice, muscle atrophy-induced mice, and muscle atrophy-treated mice. As shown in FIG. 4, the highest relative expression levels of muscle protein-destroying genes (myostatin, atrogin-1, and MuRF1) and lowest relative expression levels of muscle protein-producing genes (MyoD and myogenin) were observed in the muscle tissues of the muscle atrophy-induced mice. In contrast, the lowest relative expression levels of muscle protein-destroying genes (myostatin, atrogin-1, and MuRF1) and highest relative expression levels of muscle protein-producing genes (MyoD and myogenin) were observed in the muscle tissues of the muscle atrophy-treated mice.

Example 5: Effect of Exendin-4 on Expression Levels of Muscle Atrophy-Related Genes at Cell Level A myoblast cell line C2C12 was differentiated into myocytes by culturing in a medium containing 2% (v/v) horse serum for 5 days. Control myocytes (control) prepared from the differentiated myocytes without any treatment, myocytes in which muscle atrophy symptoms were induced by treatment of 1 μM dexamethasone for 12 hours, comparative myocytes treated with 20 nM exendin-4 for 6 hours, and experimental myocytes in which muscle atrophy symptoms were treated with 20 nM exendin-4 for 6 hours following treatment of 1 μM dexamethasone for 12 hours were each prepared. Expression levels of muscle atrophy-related genes (myostatin, atrogin-1, and MuRF1) were compared in each of the myocytes (FIG. 5).

Figure 5:
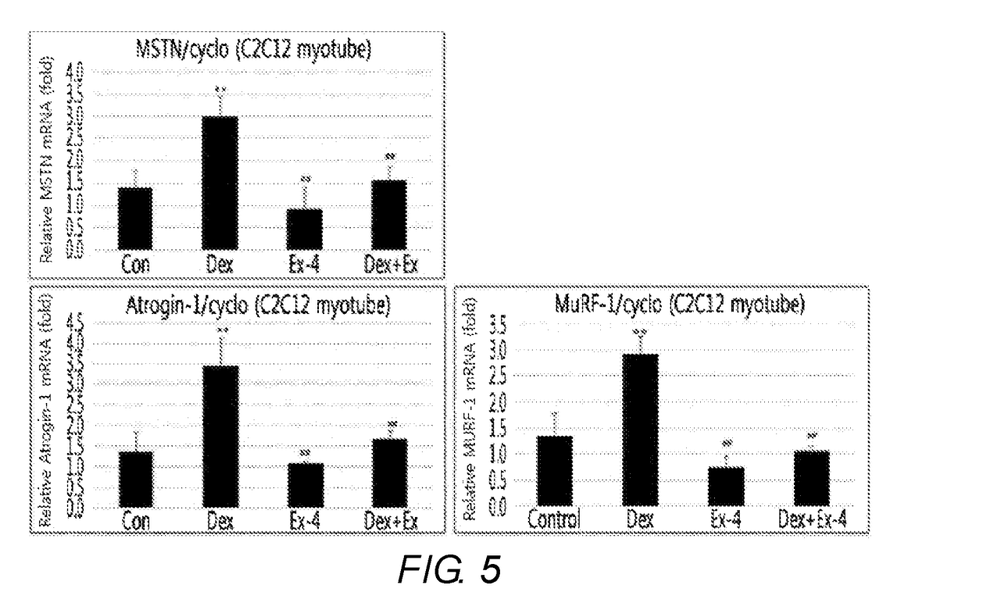
FIG. 5 is a graph showing results of comparing expression levels of muscle atrophy-related genes (myostatin, atrogin-1, and MuRF1) in control myocytes, muscle atrophy symptom-induced myocytes, comparative myocytes, and muscle atrophy symptom-treated myocytes.
Figure 6:
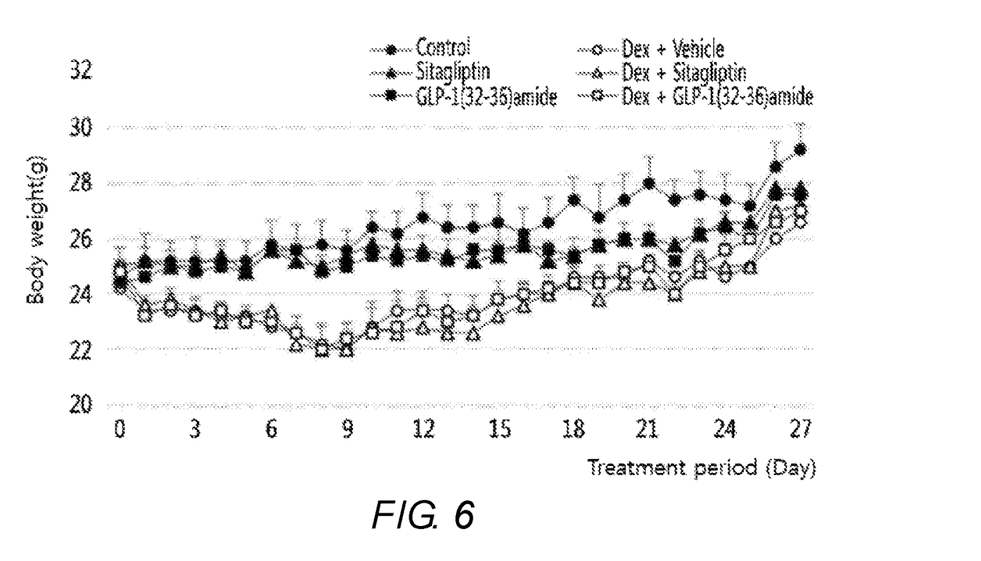
FIG. 6 is a graph showing changes in body weights of mice by sitagliptin and GLP-1(32-36)amide.
Figure 7:
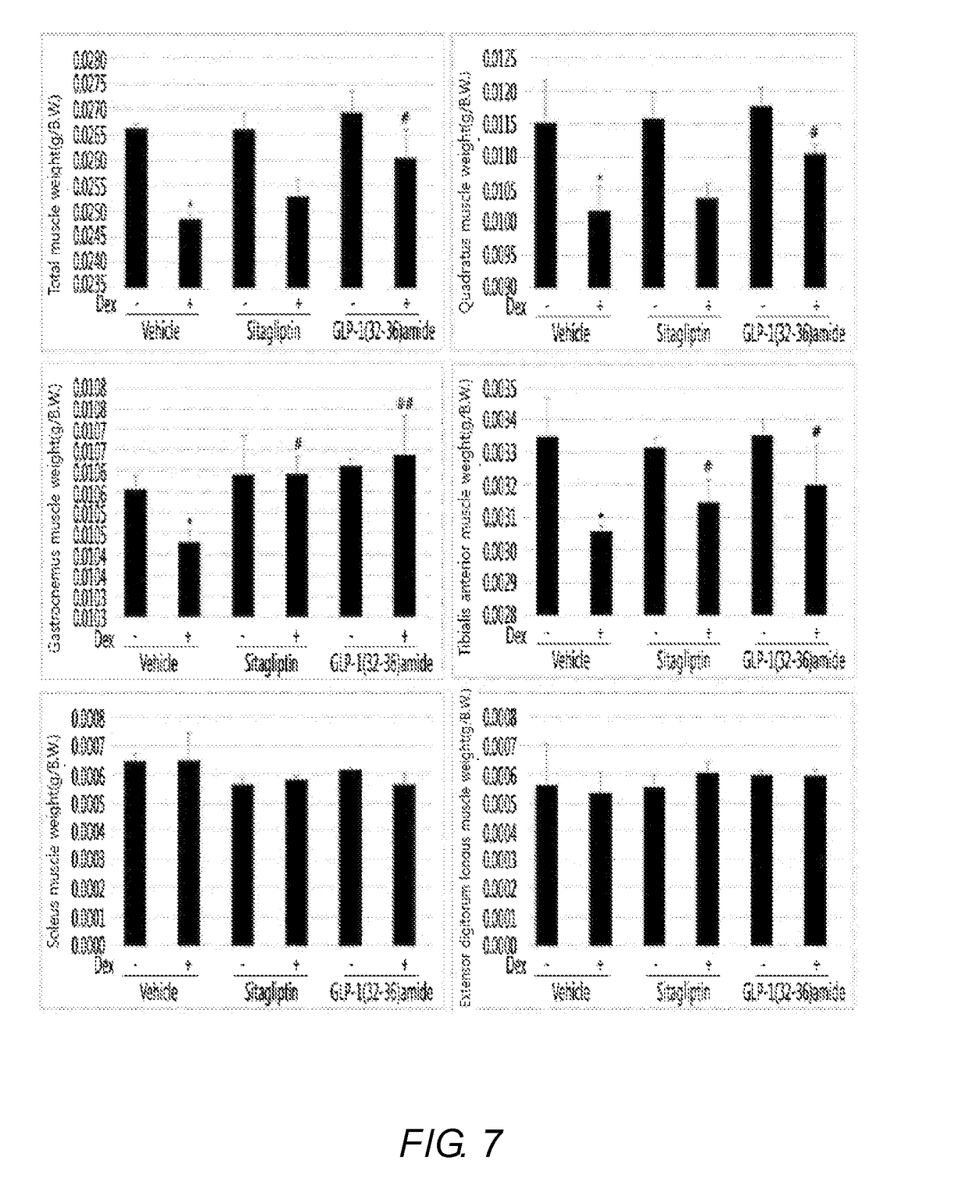
FIG. 7 is a graph showing changes in muscle weights of mice by sitagliptin and GLP-1(32-36)amide.

FIG. 5 is a graph showing results of comparing expression levels of muscle atrophy-related genes (myostatin, atrogin-1, and MuRF1) in control myocytes, muscle atrophy symptom-induced myocytes, comparative myocytes, and muscle atrophy symptom-treated myocytes. As shown in FIG. 5, the highest relative expression levels of the genes (myostatin, atrogin-1, and MuRF1) were observed in the muscle atrophy symptom-induced myocytes. In contrast, the muscle atrophy symptom-treated myocytes showed remarkably decreased expression levels of the genes (myostatin, atrogin-1, and MuRF1), similar to the levels of the control myocytes.

Taken together, the results of Examples 1 to 5 show that exendin-4 exhibits the effects of treating, improving, or recovering dexamethasone-induced muscle atrophy or sarcopenia.

Furthermore, the present inventors intended to investigate therapeutic effects of GLP-1 degradation inhibitor and GLP-1 fragment on muscle atrophy or sarcopenia, in addition to exendin-4. Thus, changes of the body weight, muscle, grip strength, and genes by sitagliptin, which is known as a GLP-1 degradation inhibitor, and GLP-1(32-36)amide were examined in animal models.

Example 6: Effects of Sitagliptin and GLP-1(32-36)Amide on Body Weight and Muscle of Muscle Atrophy Animal Model The present inventors treated C57BL/6J male mice (n=10/group) with dexamethasone (20 mg/kg/i.p.) to reduce muscles of the mice, and they examined effects of sitagliptin (300 mg/kg/oral gavage) and GLP-1(32-36)amide (5 μg/kg/ i.p.) on the body weights and muscles of the mice.

As a result, it was found that the body weight (FIG. 6) and muscle mass (FIG. 7) reduced by dexamethasone were increased by sitagliptin or GLP-1(32-36)amide.

Example 7: Effects of Sitagliptin and GLP-1(32-36)Amide on Body Weight and Muscle of Muscle Atrophy Animal Model The present inventors confirmed in Example 6 that the body weight and muscle mass were increased by sitagliptin, and accordingly, they also examined whether grip strengths of the mice were increased in order to examine whether muscle functions were actually increased by the increased body weight and muscle mass.

In detail, the grip strength when all of the paws of the mouse of Example 6 were pulled with the same force was measured by a grip strength machine.

Figure 8:
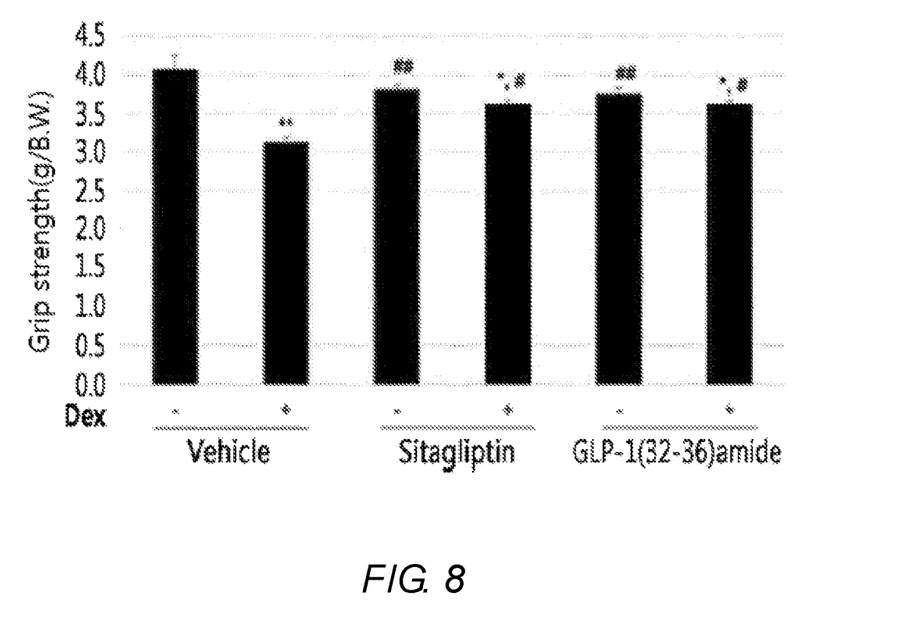
FIG. 8 is a graph showing changes in grip strengths of mice by sitagliptin and GLP-1(32-36)amide.

As a result, it was found that grip strength reduced by dexamethasone was increased again by sitagliptin and GLP-1(32-36)amide (FIG. 8).

Example 8: Effects of Sitagliptin and GLP-1(32-36)Amide on Body Weight and Muscle of Muscle Atrophy Animal Model As described above, muscle atrophy is caused by increased expression of genes destroying proteins constituting muscles and inhibited expression of genes producing the proteins.

Therefore, the present inventors examined a change in the expression level of myostatin, which is a cause of muscle atrophy, and a change in the expression level of the muscle-producing factor MyoD by sitagliptin and GLP-1(32-36) amide.

Figure 9:
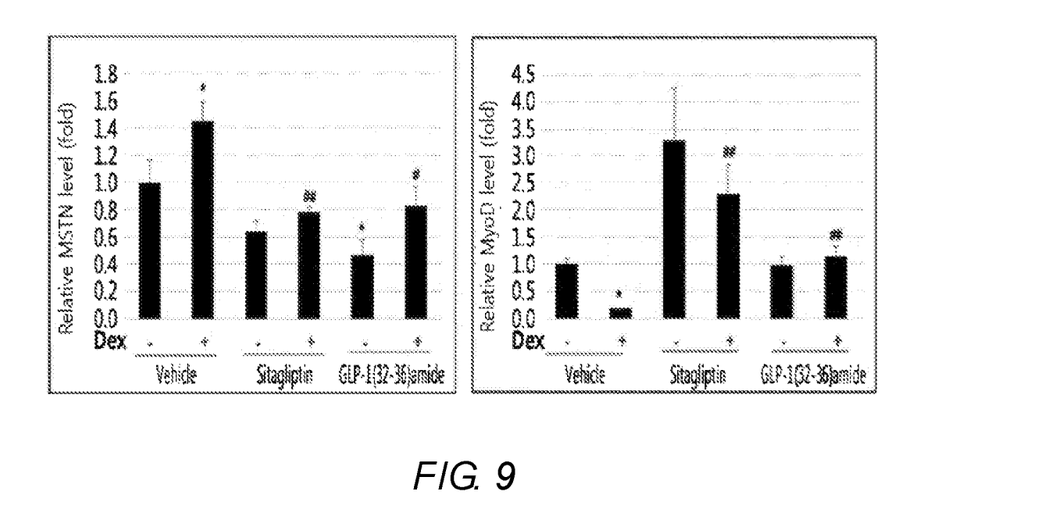
FIG. 9 is a graph showing changes in myostatin and MyoD expression by sitagliptin and GLP-1(32-36)amide.

As a result, myostatin expression was increased by dexamethasone, but decreased again by sitagliptin and GLP-1(32-36)amide. In contrast, MyoD expression was decreased by dexamethasone, but increased again by sitagliptin and GLP-1(32-36)amide (FIG. 9).

From the results of Examples 6 to 8, the present inventors confirmed that the GLP-1 degradation inhibitor sitagliptin or the GLP-1 fragment GLP-1(32-36)amide as well as GLP-1 has the therapeutic effect on sarcopenia or muscle atrophy.

Based on the above description, it will be understood by those skilled in the art that the present invention may be implemented in a different specific form without changing the technical spirit or essential characteristics thereof. Therefore, it should be understood that the above embodiment is not imitative, but illustrative in all aspects. The scope of the invention is defined by the appended claims rather than by the description preceding them, and therefore all changes and modifications that fall within metes and bounds of the claims, or equivalents of such metes and bounds are therefore intended to be embraced by the claims.

---

The invention claimed is:

1. A method for treating muscle atrophy or sarcopenia, comprising administering a pharmaceutically effective amount of a pharmaceutical composition comprising any one selected from the group consisting of glucagon-like peptide-1 (GLP-1), a GLP-1 fragment, a GLP-1 receptor (GLP-1R) agonist, a GLP-1 secretion enhancer, a GLP-1 degradation inhibitor, and exendin-4 to a subject having muscle atrophy or sarcopenia.

2. The method of claim 1, wherein the exendin-4 consists of an amino acid sequence of SEQ ID NO: 1.

3. The method of claim 1, wherein the pharmaceutical composition exhibits an effect selected from the group consisting of effects of increasing the body weight, increasing skeletal muscle mass, increasing expression of muscle protein-producing genes, and inhibiting expression of muscle protein-destroying genes, and combinations thereof.

4. The method of claim 3, wherein the muscle protein-destroying gene is a gene encoding myostatin, atrogin-1, or MuRF1 (Muscle RING-finger protein-1).

5. The method of claim 3, wherein the muscle protein-producing gene is a gene encoding MyoD or myogenin.

6. The method of claim 1, wherein the pharmaceutical composition further comprises a pharmaceutically acceptable carrier, excipient, or diluent.

7. The method of claim 1, wherein the GLP-1 fragment consists of an amino acid sequence of SEQ ID NO: 2.

8. The method of claim 1, wherein the GLP-1 degradation inhibitor is a DPP-4 inhibitor.

9. A method for treating muscle atrophy or sarcopenia, comprising administering a pharmaceutically effective amount of a pharmaceutical composition comprising any one selected from the group consisting of glucagon-like peptide-1 (GLP-1), a GLP-1 fragment, a GLP-1 receptor (GLP-1R) agonist, a GLP-1 secretion enhancer, a GLP-1 degradation inhibitor, and exendin-4 to a subject having muscle atrophy or sarcopenia, wherein the pharmaceutical composition is administered intraperitoneally.

* * * * *